US008519090B2

(12) United States Patent
Amb et al.

(10) Patent No.: US 8,519,090 B2
(45) Date of Patent: Aug. 27, 2013

(54) CATHODICALLY COLORING YELLOW SOLUBLE ELECTROCHROMIC AND LIGHT EMITTING POLYMERS

(71) Applicant: University of Florida Research Foundation, Inc., Gainesville, FL (US)

(72) Inventors: Chad Martin Amb, Midland, MI (US); Justin Adam Kerszulis, Gainesville, FL (US); John R. Reynolds, Dunwoody, GA (US); Aubrey Lynn Dyer, Atlanta, GA (US); Emily Thompson, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/775,961

(22) Filed: Feb. 25, 2013

(65) Prior Publication Data

US 2013/0165614 A1   Jun. 27, 2013

Related U.S. Application Data

(62) Division of application No. 13/282,999, filed on Oct. 27, 2011, now Pat. No. 8,399,603.

(60) Provisional application No. 61/407,615, filed on Oct. 28, 2010.

(51) Int. Cl.
*C08G 75/00* (2006.01)

(52) U.S. Cl.
USPC .................................................. 528/377

(58) Field of Classification Search
USPC ................................................. 528/377, 380
See application file for complete search history.

(56) References Cited

U.S. PATENT DOCUMENTS

| | | | |
|---|---|---|---|
| 6,020,987 | A | 2/2000 | Baumann et al. |
| 7,746,533 | B2 | 6/2010 | Sotzing et al. |
| 7,799,932 | B2 | 9/2010 | Reynolds et al. |
| 2006/0066933 | A1 | 3/2006 | Jagt et al. |
| 2009/0203873 | A1 | 8/2009 | Sotzing |
| 2010/0328751 | A1 | 12/2010 | Kondou et al. |
| 2011/0046330 | A1* | 2/2011 | Beaujuge et al. ............. 526/257 |

FOREIGN PATENT DOCUMENTS

| | | |
|---|---|---|
| WO | WO-02-079316 A2 | 10/2002 |
| WO | WO-2009-038033 A1 | 3/2009 |
| WO | WO-2009-058877 A1 | 5/2009 |
| WO | WO-2009-117025 A1 | 9/2009 |

OTHER PUBLICATIONS

Amb, C.M. et al., "Propylenedioxythiophene (ProDOT)-phenylene copolymers allow a yellow-to-transmissive electrochrome," *Polymer Chemistry*, 2011, pp. 812-814, vol. 2, No. 4.

(Continued)

*Primary Examiner* — Shane Fang
(74) *Attorney, Agent, or Firm* — Saliwanchik, Lloyd & Eisenschenk (57) ABSTRACT

Embodiments of the invention are directed to yellow-to-transmissive conjugated polymers, a method to prepare the yellow conjugated polymers, the use of the yellow conjugated polymers in an electrochromic and/or electroluminescent device comprising neutral state primary subtractive colored conjugated polymers, and a method to prepare the device comprising the yellow conjugated polymer. The yellow conjugated polymers comprise a sequence of dioxythiophene units alternating with aromatic units, thiophene units, furan units, and/or pyrrole units. The yellow conjugated polymers are prepared by cross-condensation reactions. The yellow conjugated polymers can be soluble and preparation of the device involves deposition of the yellow conjugated polymer from solution onto a surface.

19 Claims, 7 Drawing Sheets

(56) References Cited

OTHER PUBLICATIONS

Kobayashi, N. et al., "Organic electrochromism for a new color electronic paper," *Solar Energy Materials & Solar Cells*, 2008, pp. 136-139, vol. 92.

Liou, G-S. et al., "Synthesis and Electrochemical Properties of Novel Aromatic Poly(amine-amide)s with Anodically Highly Stable Yellow and Blue Electrochromic Behaviors," *Macromolecules*, 2009, pp. 125-134, vol. 42.

Nielsen, C.B. et al., "Discrete Photopatternable π-Conjugated Oligomers for Electrochromic Devices," *J. Am. Chem. Soc.*, 2008, pp. 9734-9746, vol. 130.

Wang, F. et al., Electrochromic Linear and Star Branched Poly(3,4-ethylenedioxythiophene-didodecyloxybenzene) Polymers, *Macromolecules*, 2000, pp. 2083-2091. 33 (6).

Wang, H-M. et al., "Multicolor electrochromic poly(amide-imide)s with N,N-diphenyl-N', N'-di-4-tertbutylpheny1-1,4-phenylenediamine moieties," *Polym. Chem.*, 2010, pp. 1013-1023, vol. 1.

Levesque, I. et at., "Light-Emitting Diodes from Fluorene-Based π-Conjugated Polymers", *Chem. Mater.*, 2000, pp. 1931-1936, vol. 12.

\* cited by examiner

CATHODICALLY COLORING YELLOW SOLUBLE ELECTROCHROMIC AND LIGHT EMITTING POLYMERS

CROSS-REFERENCE TO RELATED APPLICATIONS

The present application is a divisional of U.S. patent application Ser. No. 13/282,999, filed Oct. 27, 2011, which claims the benefit of U.S. Provisional Application Ser. No. 61/407,615, filed Oct. 28, 2010, the disclosures of which are hereby incorporated by reference in their entireties, including any figures, tables, or drawings.

The subject invention was made with government support under the Air Force Office of Scientific Research, Contract No. FA9550-09-1-0320. The government has certain rights to this invention.

BACKGROUND OF INVENTION

Non-emissive display technologies using electrochromic (EC) materials are of interest for devices with the ability to be viewed in a wide variety of lighting conditions, and for large area devices that can be fabricated using convenient inexpensive printing techniques. EC materials that can display three primary colors could be used to create full color display devices where the expression of any color can be achieved through the control of the intensity of each of the primary colors. Such devices require colors that can be switched "on" or "off" rapidly. Cathodically-coloring conjugated polymers are a class of materials that can demonstrate this rapid switching and polymers have been made that strongly absorb light in the visible region of the spectrum in a neutral state and upon oxidation absorb almost exclusively NIR radiation, leaving a near colorless, highly transmissive oxidized state. The addition of the colors red, green, and blue has been explored for displays from conjugated polymers; however, for truly non-emissive displays a primary subtractive color set, red, yellow and blue (RYB) or cyan, magenta and yellow (CMY), must be employed to produce all colors. Kobayashi et al., *Solar Energy Materials and Solar Cells*, 2008, 92, 136-9 has demonstrated a display from primary subtractive colored molecular electrochromic species, but the color system requires a very high potential (−2 V vs. Ag/AgCl) for switching and requires more than ten seconds and the sub-second switching speeds needed for device applications is not possible. Additionally, some colors are not stable to repeated switching.

The lack of yellow cathodically coloring conjugated polymers with band gaps of about 2.3 to about 2.8 eV has limited the development of multicolor display prototypes using primary subtractive colored conjugated polymers. The high band gap required to achieve a yellow color has prohibited switching from visible absorption bands in the neutral state to a transmissive NIR absorbing state upon oxidation. A few anodically coloring yellow conjugated polymers have been produced, Liou et al., *Macromolecules*, 2008, 42, 125-34 and Wang et al., *Polymer Chemistry*, 2010, 1, 1013-23. Although, in principle these conjugated polymers can be incorporated into display devices, in practice very specific potentials are required to achieve a yellow color without a brownish hue and these anodically coloring conjugated polymers have not displayed the potential for long term stability. The best electrochromic material that displays a yellow color consists of a conjugated oligomer containing pendant acrylate groups that can be synthesized and patterned by a UV mediated process, Nielsen et al., *Journal of the American Chemical Society*, 2008, 130, 9734-46. The conjugated oligomer segments of the polyacrylate switch from a yellow neutral state to an intense blue cation radical state and ultimately a less intense but still strongly blue dicationic state.

A yellow to transmissive cathodically coloring conjugated polymer is very desirable as it is the only color missing from the primary subtractive colored conjugated polymers. A non-emissive conjugated polymer display having a primary subtractive color set can be produced with a yellow to transmissive cathodically coloring conjugated polymer.

BRIEF SUMMARY

Embodiments of the invention are directed to conjugated polymers having a fully conjugated polymeric sequence of at least two alternating triads of a first and second repeating unit. The first repeating units are dioxyheterocyclic units selected from one or more of dioxythiophene, dioxyfuran, dioxypyrrole, or dioxyselenophene or any combination thereof. The second repeating units are selected from aromatic, thiophene, furan, pyrrole, selenophene or any combination thereof. The conjugated polymer is yellow in its neutral state and displays an absorption maximum between 300 and 500 nm and upon oxidation is transmissive between 400-750 nm. The fully conjugated polymeric sequence can be a polymer having alternating first and second repeating units, an alternating copolymer, an ABA copolymer, or it can be a portion of a random copolymer where statistically at least two alternating triads are formed. The fully conjugated polymeric sequence can be a portion of network or of a block, graft, branched, hyperbranched, or dendritic copolymer.

In an embodiment of the invention, the yellow conjugated polymer or a polymeric precursor of the conjugated polymer can be soluble in at least one solvent, which permits deposition of a film of the polymer from solution. In one embodiment, a thin film comprising the conjugated polymer in the neutral state can display a transmittance of less than about 40% between 400 nm and 500 nm and greater than about 90% transmittance from 600 nm-750 nm, and can undergo oxidation to a transmissive state having a transmittance of more than about 70% between 400 and 750 nm. The yellow conjugated polymer can be electrochromic and/or electroluminescent.

Another embodiment of the invention is directed to the preparation of the yellow conjugated polymer by cross-coupling nucleophilic monomeric units with electrophilic monomeric units to yield the conjugated polymer or a precursor of the conjugated polymer. Cross-coupling can be a Stille coupling, Kumada coupling, Hiyama coupling, Negishi coupling, Suzuki coupling, or Grignard methathesis (GRIM).

Other embodiments of the invention are directed to electrochromic, electroluminescent, and/or combined electrochromic, electroluminescent devices comprising the yellow conjugated polymer. When combined with other electrochromic polymers (conjugated polymers) having other primary subtractive colors in a neutral state and are transmissive in an oxidized state a full color device can be achieved.

DETAILED DISCLOSURE

Embodiments of the invention are directed to yellow-to-transmissive switching cathodically coloring conjugated polymers, their preparation and displays having a palette of primary subtractive colors prepared with these neutral state yellow conjugated polymers. The yellow conjugated polymers exhibit high optical contrasts at the wavelength of peak absorption in the neutral state, which upon oxidation become highly transmissive throughout the entire visible region. For purposes of the invention, high transmissivity of a conjugated polymer is considered to be achieved when a film can be switched from transmittance less than 40% between 400 nm and 500 nm with transmittance greater than 90% from 600 nm-750 nm, to a film which displays greater than 70% transmittance between 400 nm and 750 nm. In embodiments of the invention, the yellow conjugated polymer is soluble in at least one solvent, for example toluene, chloroform, dichloromethane, hexanes, tetrahydrofuran, chlorobenzene, water, ethanol, other solvents or combination of solvents. From solution, the soluble yellow conjugated polymer is readily incorporated into an electrochromic device using convenient deposition methods such as spin coating, spray casting, and printing techniques such as screen printing, inkjet printing, offset printing, rotogravure, slot-dye coating, or flexography to form a thin film. In embodiments of the invention, yellow-to-transmissive conjugated polymers can be included in either reflective or transmissive ECDs which use conjugated polymers of three primary colors, either red, yellow and blue (RYB) or cyan, magenta and yellow (CMY), in a complete subtractive color space to allow any color to be produced by the appropriate color combination. These complete multi-color conjugated polymer devices can be used in various display technologies such as displays for electronics, full color e-books, and signage. In other embodiments of the invention, electroluminescent or combination electroluminescent/electrochromic devices are formed, having light emitting and/or electrochromic properties.

In an embodiment of the invention, the yellow conjugated polymers are transmissive and color neutral in the oxidized state and yellow in a neutral state with peak absorption, $\lambda_{max}$, at about 450 nm, where as a thin film, the yellow conjugated polymers display less than 20% transmission between 400 and 500 nm and having an onset of absorption of 2.3-3.0 eV in the neutral state and can be converted by electrochemical reaction to a film with greater than 70% transmission throughout the visible spectrum from 400-750 nm. The yellow conjugated polymers display high optical contrast in the visible region and possess rapid switching speeds and stability upon repetitive switching. The yellow conjugated polymers can be processed from solution, which is advantageous for use in reflective and transmissive electrochromic devices (ECDs), electroluminescent devices, or combination electroluminescent/electrochromic devices.

Figure 1:
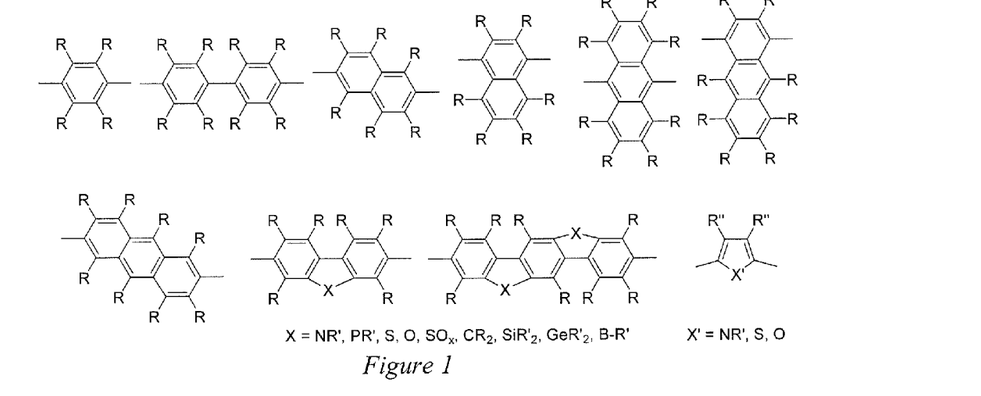
FIG. 1 shows various aromatic and heterocyclic repeating units that can be the second repeating unit of an alternating sequence of the yellow conjugated polymer according to an embodiment of the invention.

Embodiments of the invention are directed to yellow conjugated polymers that comprise portions of a polymer that have a fully conjugated polymer sequence of alternating repeating units where a first repeating unit is a dioxyheterocyclic unit that alternates with a second repeating unit that is a substituted or unsubstituted aromatic unit or heterocyclic unit other than a dioxysubstituted heterocyclic unit. The dioxyheterocyclic units can be 3,4-alkylenedioxythiophenes, 3,4-alkylenedioxyselenophenes, 3,4-alkylenedioxypyrroles, 3,4-alkylenedioxyfurans, which are substituted on the alkylene bridge, 3,4-dialkoxythiophenes, 3,4-dialkoxyselenophenes, 3,4-dialkoxypyrroles, 3,4-dialkoxyfurans, or any combination thereof, where pyrrole rings are either unsubstituted or substituted, for example, with alkyl groups and alkyl groups that are further substituted. Aromatic units can be unsubstituted or substituted with alkyl groups that may be further substituted in any manner that does not change the conjugation of the base group or introduce an additional colored moiety, for example the further substitution can include but is not limited to: alkene, alkyne, ether, ester, amide, carboxylic acid, sulfonate, or amine functionalized chains. The alkyl groups can be linear, branched, or cyclic in structure. Of the second repeating units, aromatic units include, but are not limited to, 1,4-phenylenes, biphenylenes, fullerenes, naphthalenes, anthracenes, or combinations thereof. Some exemplary aromatic units are included in FIG. 1. The R groups, for the structures shown in FIG. 1, can be, independently, H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, hydroxy, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $CO_2H$, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $NH_2$, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$ alkynylamino, $C_8$-$C_{30}$ (arylalkenyl) amino, $C_8$-$C_{30}$ (arylalkynyl)amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$ aryl(alkyl)amino, $C_7$-$C_{30}$ di(arylalkyl)amino, $C_8$-$C_{30}$ alkyl(arylalkyl)amino, $C_{15}$-$C_{30}$ aryl(arylalkyl)amino, $C_8$-$C_3$-$C_{30}$ alkenyl(aryl)amino, $C_8$-$C_{30}$ alkynyl(aryl)amino, C(O)NH$_2$ (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$ diarylamido, $C_8$-$C_{30}$ aryl(alkyl)amido, $C_{15}$-$C_{30}$ di(arylalkyl)amido, $C_9$-$C_{30}$ alkyl(arylalkyl)amido, $C_{16}$-$C_{30}$ aryl(arylalkyl)amido, thiol, C hydroxyalkyl, $C_6$-$C_{14}$ hydroxyaryl, $C_7$-$C_{30}$ hydroxyarylalkyl, $C_3$-$C_{30}$ hydroxyalkenyl, $C_3$-$C_{30}$ hydroxyalkynyl, $C_8$-$C_{30}$ hydroxyarylalkenyl, $C_8$-$C_{30}$ hydroxyarylalkynyl, $C_3$-$C_{30}$ polyether, $C_3$-$C_{30}$ polyetherester, $C_3$-$C_{30}$ polyester $C_3$-$C_{30}$ polyamino, $C_3$-$C_{30}$ polyaminoamido, $C_3$-$C_{30}$ polyaminoether, $C_3$-$C_{30}$ polyaminoester, $C_3$-$C_{30}$ polyamidoester, $C_3$-$C_{30}$alkylsulfonic acid, $C_3$-$C_{30}$alkylsulfonate salt, $C_1$-$C_{30}$ carboxylate salt, thiocarboxylate salt, dithiocarboxylate salt or $C_3$-$C_{30}$alkyl$C_1$-$C_4$ trialkyammonium salt. The R' groups, in the repeating units of FIG. 1, can be, independently, H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_1$-$C_{30}$ hydroxyalkyl, $C_6$-$C_{14}$ hydroxyaryl, $C_7$-$C_{30}$ hydroxyarylalkyl, $C_3$-$C_{30}$ hydroxyalkenyl, $C_3$-$C_{30}$ hydroxyalkynyl, $C_8$-$C_{30}$ hydroxyarylalkenyl, $C_8$-$C_{30}$ hydroxyarylalkynyl, $C_3$-$C_{30}$ polyether, $C_3$-$C_{30}$ polyetherester, $C_3$-$C_{30}$ polyester $C_3$-$C_{30}$ polyamino, $C_3$-$C_{30}$ polyaminoamido, $C_3$-$C_{30}$ polyaminoether, $C_3$-$C_{30}$ polyaminoester, $C_3$-$C_{30}$ polyamidoester, $C_3$-$C_{30}$alkylsulfonic acid, $C_3$-$C_{30}$alkylsulfonate salt, $C_1$-$C_{30}$ alkylcarboxylate salt, $C_1$-$C_{30}$ alkylthiocarboxylate salt, $C_1$-$C_{30}$ alkyldithiocarboxylate salt or $C_3$-$C_{30}$ alkyl $C_f$-$C_f$ trialkyammonium salt. The R" groups, in the repeating units of FIG. 1, can be, independently, H, $C_1$-$C_{30}$ alkyl, $C_3$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl. The R" groups that are not H have sp$^3$ hybridized carbons attached to the heterocyclic ring. Alkyl groups can be straight, branched, multiply branched, cyclic, or polycyclic where cyclic and polycyclics can be unsubstituted, substituted, or polysubstituted, alkenyl can be a monoene, conjugated or non-conjugated polyene, straight, branched, multiply branched, cyclic, or polycyclic, terminal or internal, substituted at any carbon, E or Z isomers or mixture thereof, alkynes can be mono-yne, conjugated or non-conjugated poly-yne, terminal or internal, substituted at any carbon, aryl groups can be cyclic, fused or unfused polycyclic of any geometry, asymmetric functional groups, such as ester and amido, can have either orientation with respect to the alkylenedioxythiophene rings, poly can be 2 or more. Heteroatoms in substituents $R^1$-$R^8$ can be at any position of those substituents. For example an oxygen of an ether or ester or a nitrogen of an amine or amide can be in the alpha, beta, gamma or any other position relative to the point of attachment to the aromatic groups. Heteroatom containing substituents can have a plurality of heteroatoms, for example ether can be a monoether, a diether or a polyether, amine can be a monoamine, a diamine or a polyamine, ester can be a monoester, a diester, or a polyester, and amide can be a monoamide, a diamide or a polyamide. Ethers and esters groups can be thioethers, thioesters and hydroxy groups can be thiol (mercapto) groups, where sulfur is substituted for oxygen. Salts can be those of alkali or alkali earth metals, ammonium salts, or phosphonium salts.

Figure 2:
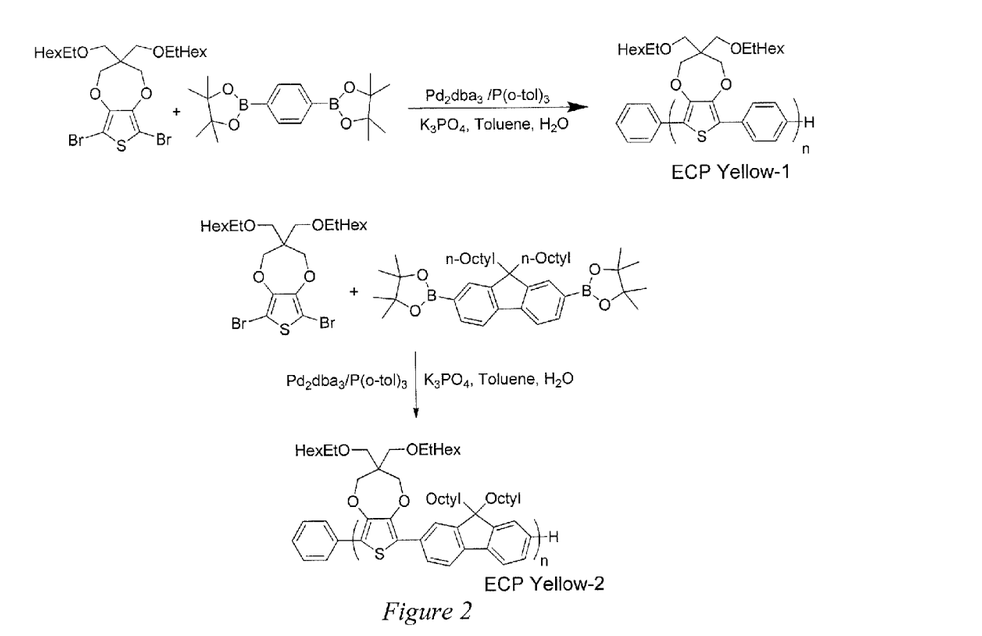
FIG. 2 shows a reaction scheme for the preparation of exemplary yellow conjugated polymers, ECP Yellow-1 and ECP Yellow-2, by a Suzuki condensation, according to an embodiment of the invention.

In some embodiments of the invention, the alternating polymeric sequence can be a polymer, such as that shown in FIG. 2, which can be viewed as a condensation homopolymer of two complementary monomers. Copolymers can be made where first repeating units can include a plurality of different dioxyheterocyclic units and the second repeating units can include a purality of different aromatic or heterocyclic units. As can be appreciated by those skilled in the art, a linear polymeric sequence of this type is readily formed by the condensation of appropriately substituted difunctional monomers where the different alternating units are from monomers with complementary reactive functionality. The use of monofunctional and/or trifunctional monomers of one or more of the alternating units allows the control of the molecular weight, branching, hyperbranching, and network formation of the yellow conjugated polymers, and one or more repeating unit can be appropriately substituted to be monofunctional toward formation of the alternating sequence and allow formation of various different kinds of block copolymers simultaneously or sequentially where the block copolymer contains a yellow conjugated polymer block.

In embodiments of the invention, the yellow conjugated polymer can be a random copolymer of three or more repeating units where the polymer has a sequence of at least two alternating triads (series of three repeating units) that can be either a first unit-second unit-first unit triad or a second unit-first unit-second unit triad. The additional repeating units may increase the conjugation beyond the triad or may be a repeating unit that does not increase the conjugation length beyond the triad. As can be appreciated by those skilled in the art, to permit formation of a film that has sufficient color intensity, the use of a thin film requires a greater proportion of the yellow conjugated polymer portions having the alternating triads than does a thicker film.

In embodiments of the invention, a yellow conjugated polymer has the alternating first and second repeating unit sequence of the structure:

(I)

where: A is an aromatic unit, thiophene unit, furan unit, pyrrole unit, selenophene, or any combination thereof; n is 2 to 200,000; x is 0 or 1; y is 0 or 1; X is S, Se, O, or NR; R is H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_1$-$C_{30}$ hydroxyalkyl, $C_6$-$C_{14}$ hydroxyaryl, $C_7$-$C_{30}$ hydroxyarylalkyl, $C_3$-$C_{30}$ hydroxyalkenyl, $C_3$-$C_{30}$ hydroxyalkynyl, $C_8$-$C_{30}$ hydroxyarylalkenyl, $C_8$-$C_{30}$ hydroxyarylalkynyl, $C_3$-$C_{30}$ polyether, $C_3$-$C_{30}$ polyetherester, $C_3$-$C_{30}$ polyester $C_3$-$C_{30}$ polyamino, $C_3$-$C_{30}$ polyaminoamido, $C_3$-$C_{30}$ polyaminoether, $C_3$-$C_{30}$ polyaminoester, $C_3$-$C_{30}$ polyamidoester $C_3$-$C_{30}$alkylsulfonic acid, $C_3$-$C_{30}$alkylsulfonate salt, $C_1$-$C_{30}$ alkylcarboxylate salt, $C_1$-$C_{30}$ alkylthiocarboxylate salt, $C_1$-$C_{30}$ alkyldithiocarboxylate salt or $C_3$-$C_{30}$ alkyl $C_1$-$C_4$ trialkyammonium salt; and $R^1$, $R^2$, $R^3$, $R^4$, $R^5$, $R^6$, $R^7$ and $R^8$ are independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, hydroxy, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_5$-$C_{30}$ arylalkenyloxy, $C_8$-$C_{30}$ arylalkynyloxy, $C_2$-$C_{14}$, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $NH_2$, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$ alkynylamino, $C_8$-$C_{30}$ (arylalkenyl)amino, $C_8$-$C_{30}$ (arylalkynyl) amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$ aryl(alkyl) amino, $C_7$-$C_{30}$ di(arylalkyl)amino, $C_8$-$C_{30}$ alkyl(arylalkyl) amino, $C_{15}$-$C_{30}$ aryl(arylalkyl)amino, $C_8$-$C_{30}$ alkenyl(aryl) amino, $C_8$-$C_{30}$ alkynyl(aryl)amino, $C(O)NH_2$ (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$ diarylamido, $C_8$-$C_{30}$ aryl(alkyl)amido, $C_{15}$-$C_{30}$ di(arylalkyl)amido, $C_9$-$C_{30}$ alkyl(arylalkyl)amido, $C_{16}$-$C_{30}$ aryl(arylalkyl)amido, thiol, $C_1$-$C_{30}$ hydroxyalkyl, $C_6$-$C_{14}$ hydroxyaryl, $C_7$-$C_{30}$ hydroxyarylalkyl, $C_3$-$C_{30}$ hydroxyalkenyl, $C_3$-$C_{30}$ hydroxyalkynyl, $C_8$-$C_{30}$ hydroxyarylalkenyl, $C_8$-$C_{30}$ hydroxyarylalkynyl, $C_3$-$C_{30}$ polyether, $C_3$-$C_{30}$ polyetherester, $C_3$-$C_{30}$ polyester, $C_3$-$C_{30}$ polyamino, $C_3$-$C_{30}$ polyaminoamido, $C_3$-$C_{30}$ polyaminoether, $C_3$-$C_{30}$ polyaminoester, $C_3$-$C_{30}$ polyamidoester, $C_3$-$C_{30}$alkylsulfonic acid, $C_3$-$C_{30}$alkylsulfonate salt, $C_1$-$C_{30}$ carboxylate salt, thiocarboxylate salt, dithiocarboxylate salt or $C_3$-$C_{30}$alkyl$C_1$-$C_4$ trialkyammonium salt. Alkyl groups can be straight, branched, multiply branched, cyclic, or polycyclic where cyclic and polycyclics can be unsubstituted, substituted, or polysubstituted, alkenyl can be a monoene, conjugated or non-conjugated polyene, straight, branched, multiply branched, cyclic, or polycyclic, terminal or internal, substituted at any carbon, E or Z isomers or mixture thereof, alkynes can be mono-yne, conjugated or non-conjugated poly-yne, terminal or internal, substituted at any carbon, aryl groups can be cyclic, fused or unfused polycyclic of any geometry, asymmetric functional groups, such as ester and amido, can have either orientation with respect to the alkylenedioxythiophene rings, poly can be 2 or more. Heteroatoms in substituents $R^1$-$R^8$ can be at any position of those substituents. For example an oxygen of an ether or ester or a nitrogen of an amine or amide can be in the alpha, beta, gamma or any other position relative to the point of attachment to the 3,4-alkylenedioxythiophene. Heteroatom containing substituents can have a plurality of heteroatoms, for example, ether can be a monoether, a diether or a polyether, amine can be a monoamine, a diamine or a polyamine, ester can be a monoester, a diester, or a polyester, and amide can be a monoamide, a diamide or a polyamide. Ethers and esters groups can be thioethers, thioesters and hydroxy groups can be thiol (mercapto) groups, where sulfur is substituted for oxygen. In one embodiment of the invention, x is 1, y is 0, and $R^1$, $R^2$, $R^5$ and $R^6$ are hydrogen and $R^3$=$R^4$H. In one embodiment of the invention x is 1, y is 0, and $R^1$, $R^2$, $R^5$ and $R^6$ are hydrogen and $R^3$=$R^4$=$CH_2OR$ where R is an alkyl group. Salts can be those of alkali or alkali earth metals, ammonium salts, or phosphonium salts.

In other embodiments of the invention a yellow conjugated polymer has an alternating sequence of first and second repeating units of the structure:

(II)

where A is an aromatic unit, thiophene unit, furan unit, pyrrole unit, selenophene unit, or any combination thereof; n is 2 to 200,000; X is S, Se, O, or NR; where R, $R^9$ and $R^{10}$ are independently H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $NH_2$, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$ alkynylamino, $C_8$-$C_{30}$ (arylalkenyl)amino, $C_8$-$C_{30}$ (arylalkynyl) amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$ aryl(alkyl) amino, $C_7$-$C_{30}$ di(arylalkyl)amino, $C_8$-$C_{30}$ alkyl(arylalkyl) amino, $C_{15}$-$C_{30}$ aryl(arylalkyl)amino, $C_8$-$C_{30}$ alkenyl(aryl) amino, $C_8$-$C_{30}$ alkynyl(aryl)amino, $C(O)NH_2$ (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$ diarylamido, $C_8$-$C_{30}$ aryl(alkyl)amido, $C_{15}$-$C_{30}$ di(arylalkyl)amido, $C_9$-$C_{30}$ alkyl(arylalkyl)amido, $C_{16}$-$C_{30}$ aryl(arylalkyl)amido, thiol, $C_1$-$C_{30}$ alkylhydroxy, $C_6$-$C_{14}$ arylhydroxy, $C_7$-$C_{30}$ arylalkylhydroxy, $C_3$-$C_{30}$ alkenylhydroxy, $C_3$-$C_{30}$ alkynylhydroxy, $C_8$-$C_{30}$ arylalkenylhydroxy, $C_8$-$C_{30}$ arylalkynylhydroxy, $C_3$-$C_{30}$ polyether, $C_3$-$C_{30}$ polyetherester, $C_3$-$C_{30}$ polyester $C_3$-$C_{30}$ polyamino, $C_3$-$C_{30}$ polyaminoamido, $C_3$-$C_{30}$ polyaminoether, $C_3$-$C_{30}$ polyaminoester, $C_3$-$C_{30}$ polyamidoester, $C_3$-$C_{30}$ alkylsulfonic acid, $C_3$-$C_{30}$ alkylsulfonate salt, or $C_3$-$C_{30}$ alkyl$C_1$-$C_4$ trialkyammonium salt. Alkyl groups can be straight, branched, multiply branched, cyclic, or polycyclic where cyclic and polycyclics can be unsubstituted, substituted, or polysubstituted, alkenyl can be a monoene, conjugated or non-conjugated polyene, straight, branched, multiply branched, cyclic, or polycyclic, terminal or internal, substituted at any carbon, E or Z isomers or mixture thereof, alkynes can be mono-yne, conjugated or non-conjugated poly-yne, terminal or internal, substituted at any carbon, aryl groups can be cyclic, fused or unfused polycyclic of any geometry, asymmetric functional groups, such as ester and amido, can have either orientation with respect to the 3,4-dioxythiophene rings, poly can be 2 or more. Heteroatoms in substituents $R^1$ and $R^2$ can be at any reasonable position of those substituents. For example an oxygen of an ether or ester or a nitrogen of an amine or amide can be in the beta, gamma or any other position relative to the point of attachment to the 3,4-dioxythiophene, but not the alpha position. Heteroatom containing substituents can have a plurality of heteroatoms, for example ether can be a monoether, a diether or a polyether, amine can be a monoamine, a diamine or a polyamine, ester can be a monoester, a diester, or a polyester, and amide can be a monoamide, a diamide or a polyamide. Ethers and esters groups can be thioethers, thioesters and hydroxy groups can be thiol (mercapto) groups, where sulfur is substituted for oxygen. Salts can be those of alkali or alkali earth metals, ammonium salts, or phosphonium salts.

In embodiments of the invention the yellow conjugated polymer sequence is a portion of a block copolymer, graft copolymer, or polymer network where non-conjugated polymer portion(s) can be any polymer that can be prepared by a step-growth or chain-growth process. For example, as can be appreciated by one skilled in the art, a triblock copolymer can be formed where a non-coloring polymer mono-terminated with either or both of the alternating units can be employed as end-capping monofunctional units in a condensation polymerization with a plurality of difunctional monomers for the yellow conjugated polymer's alternating sequence containing portion according to an embodiment of the invention. In another embodiment of the invention, a non-conjugated polymer can be terminated at both ends with one of either of the monomers for the alternating EC portion to form a multiblock polymer upon condensation with the appropriate proportions of the two monomers for the yellow conjugated polymer portion. In another embodiment of the invention a non-conjugated polymer with substitution of one of the complementary monomers of the conjugated polymer portion can be condensed with yellow conjugated polymer forming monomers to yield graft-like or network copolymers. The yellow conjugated polymer segments can be formed before, during or after the formation of the non-conjugated polymer portion of block copolymers, as can be appreciated by one skilled in the art.

In embodiments of the invention, the yellow conjugated polymer can be transformed into a different polymer, by reactions on the conjugated polymer portion. For example, but not limited to, the reaction can be a transformation of the substituents on one or more of the alternating repeating units. In some embodiments of the invention the yellow conjugated polymer can contain, for example, a reactive ProDOT of structure, as shown in structure I above, where $R^1$ through $R^6$ groups permit processing of the yellow conjugated polymer into a film that can be subsequently converted to a different yellow conjugated polymer and, for example, a soluble film can be converted into an insoluble film. For example, where $R^3$ and $R^4$ are di-ester groups, conversion to carboxylic acid groups can be carried out in the manner disclosed in Reynolds et al. U.S. Pat. No. 7,799,932, Sep. 21, 2010, and incorporated by reference herein. If desired, the di-acid can be subsequently converted into a carboxylate salt. Reactions can also involve one or more units of the other polymeric segments of block copolymers other than those of the conjugated polymer portion. Repeating units or terminal ends of the yellow conjugated polymer can be substituted to promote self associate or cross-associate with plurally functional additives to form a super-molecular structure through non-covalent interactions such as hydrogen bonding, ion-dipole, ion pairing, ion chelation, dipole-dipole, or other non-covalent bonding forces. For example, some repeating units may be substituted with specific polyol groups that are readily solvated by a solvent, but strongly associate specifically with one or more other polyol groups of the yellow conjugated polymer or of an additive upon removal of the solvent to form a super-molecular yellow conjugated polymer complex. In some embodiments of the invention, the polymer having a yellow conjugated polymer portion can be cross-linked, for example after deposition on a surface that will be part of a device, for example, an electrochromic device. For example, repeating units of the polymer can have a functional group that can be induced to add to or condense with another group upon activation or initiation that is within the conjugated polymer or on a reagent that is difunctional or polyfunctional that is added to the yellow conjugated polymer. For example vinyl units can be induced to undergo vinyl addition, cyclic groups can be induced to undergo ring-opening addition, or complementary groups can undergo catalyzed addition or condensation to form a network. Functionalities that can be employed can be appreciated by those skilled in the art. For example, a precursor to a yellow conjugated polymer network can be deposited on a surface from solution and a catalyst, a reagent, heat or radiation can be used to cause network formation. In many cases a precursor to a yellow conjugated polymer network is a non-network yellow conjugated polymer according to an embodiment of the invention.

Other embodiments of the invention are directed to a method of preparing the yellow conjugated polymer by cross-coupling reaction of an electrophilic 3,4-alkylenedioxythiophene substituted on the alkylene bridge (I) or 3,4-dialkoxythiophene unit (II) and a nucleophilic aromatic donor unit by a Suzuki condensation; a specific example of this condensation is shown in FIG. 2. The present method allows sufficient molecular weight where the fully conjugated limit of the pi to pi* transition is reached and the polymer can be solution processable as a film yellow conjugated polymers because reliable purifications of the nucleophilic monomer and the electrophilic monomer can be effectively carried out. As with virtually all cross-coupling step-growth polymerizations, the degree of polymerization for yellow conjugated polymers is limited by any deviation from stoichiometry. Hence the purity of both monomers is critical to achieving a sufficiently large polymer for use in many viable electrochromic devices. The electrophilic monomers are substituted with leaving groups such as halogens, triflates, tosylates, mesylates, nosylates, trifluoroacetates or other substituted sulfonates that can act as the leaving group. In some embodiments of the invention the nucleophilic monomers can be substituted with tin or zinc moieties rather than boron moieties as shown in FIG. 2. Coupling reactions that can be used for the preparation of the yellow conjugated polymers, include, but are not restricted to: Suzuki coupling, Stille coupling, Kumada coupling, Hiyama coupling, Negishi coupling, and Grignard methathesis (GRIM).

In embodiments of the invention the yellow conjugated polymer sequence can have structure I, where x is 1 and y is 0, which is a substituted propylene bridge of, for example, a PropOT-A yellow conjugated polymer where variations in the composition permit the tuning of the electrochromic features and permit a desired device fabrication method. In some embodiments of the invention the substituents comprise non-polar side chains. In other embodiments the substituents comprise polar or ionic side chains, including but not exclusive to: ether, ester, amide, carboxylic acid, sulfonate, and amine functionalized chains. By the incorporation of polar or ionic substituents, the yellow conjugated polymers can be designed to adsorb on metal or metal oxide surfaces, for example, but not limited to, titania for use in solar cells (Graetzel Cells) or other devices. An electrochromic device can be formed by a layer-by-layer deposition process when a substituent that imparts solubility to the yellow conjugated polymer is included with one or more other conjugated polymers that provide one or more different colors. In an embodiment of the invention, an ED displays all colors by the subtractive color mixing of Cyan Magenta Yellow (CMYK) or Red Yellow Blue (RYB) conjugated polymers employing the yellow conjugated polymer, according to an embodiment of the invention. The desired colors can be achieved by: sequentially patterning the multiple colors (CMY or RYB) in a layered fashion to achieve color mixing; patterning in a lateral configuration, such that the patterned pixels are small enough and close enough that the human eye sees the adjacent colors as a mixture; or stacking as films on separate electrodes to mix colors. For example, the polymers of colors red, yellow, and blue can be patterned as clusters of squares, rectangles, circles, triangles, or other regular or irregular shapes, onto patterned electrode pixels to combine the colors at each pixel and allow the resulting observed color to be any color of the visible spectrum. For example, when the red and yellow polymers are in their neutral state, and the blue polymer is in a colorless oxidized state, the pixel displays the color orange, and, when the yellow and blue pixels are in the neutral state with the red pixel in a colorless oxidized state, the displayed color is green.

The yellow conjugated polymers according to embodiments of the invention can be employed in a wide variety of applications. For example, the yellow conjugated polymer can be a component of an active layer in bulk heterojunction solar cells. The $R^1$ and $R^2$ groups of the 3,4-dialkoxythiophenes unit of polymer II can be of a structure that directs and enhances adsorption of the yellow conjugated polymer to a metal oxide through a polar carboxylate or even phosphate functionalities for use in dye sensitized solar cells, where the yellow EC polymer functions as the active light absorbing layer. Other uses for the yellow conjugated polymers according to embodiments of the invention are as charge transport layers and charge injection layers for field-effect transistor devices.

METHODS AND MATERIALS

Synthesis of a Yellow Conjugated Polymer (ECP Yellow-1)

A vial was charged with 6,8-dibromo-3,3-bis(((2-ethylhexyl)oxy)methyl)-3,4-dihydro-2H-thieno[3,4-b][1,4]di-oxepine (699.87 mg, 1.169 mmol) and transferred as a hexanes solution (10 mL) into a schlenk tube. After removal of the hexanes in vacuo, the tube was charged with 1,4-benzene diboronic acid bis(pinecol) ester (387.7 mg, 1.1748 mmol), $K_3PO_4$ (3.184 g, 0.015 mol), P(o-tol)$_3$ (20 mg, 0.06571 mmol), Pd$_2$dba$_3$ (10.7 mg, 0.01169 mmol, 1 mol % Pd/Br), and one drop of aliquat 336. The mixture was placed under vacuum for 2 hours. The tube was backfilled with argon gas, and the vacuum-purge cycle was repeated 3 times. Toluene (15 mL) and water (5 mL) were added, and the mixture was stirred at 85° C. for 3 days. After addition of 4,4,5,5-tetramethyl-2-phenyl-1,3,2-dioxaborolane (550 mg, 2.7 mmol), the mixture was stirred for 8 hours at 85° C., after which bromobenzene (0.37 mL, 3.5 mmol) was added and the mixture stirred overnight. Toluene (20 mL) was added, and the mixture was precipitated into a mixture of methanol (200 mL) and 1M HCl (25 mL). The precipitate was filtered into a 25 mm×80 mm cellulose thimble, washed 3 times with methanol (30 mL) and again three times with DI water (30 mL). The precipitate was purified by soxhlet extractions: methanol (one day), acetone (one day), hexanes (one day), and chloroform (one day). The chlorofolln soluble fraction was treated with a spatula tip amount of diethylammonium dithiocarbonate and stirred for 10 minutes and concentrated to about 50 mL. The concentrated solution was pipetted dropwise into 200 mL of HPLC grade methanol, and the resulting precipitate was filtered on a nylon filter membrane. The polymer was then collected and dried in vacuo to yield a brown solid, which forms yellow films. Yield 83% (530 mg). GPC $M_w$=42,230, $M_n$=24,968, PDI=1.69. $^1$H NMR (CDCl$_3$): δ 7.78 (br s, 4H), 4.2 (br s, 4H), 3.58 (br s, 4H), 3.36 (br s, 4H), 1.6-1.2 (br, 20H), 0.96 (br s, 14H) Anal. calcd. for $C_{38}H_{54}O_4S$ C, 72.33; H, 9.01, Found C, 72.47; H, 9.81.

Synthesis of a Yellow Conjugated Polymer (ECP Yellow-2)

A vial was charged with 6,8-dibromo-3,3-bis(((2-ethylhexyl)oxy)methyl)-3,4-dihydro-2H-thieno[3,4-b][1,4]di-oxepine (700 mg, 1.169 mmol) and transferred as a hexanes solution (10 mL) into a schlenk tube. After removal of the hexanes in vacuo, the tube was charged with 9,9-dioctylfluorene 2,7-bis-diboronic acid bis(pinecol) ester (755.34 mg, 1.1755 mmol), $K_3PO_4$ (3.184 g, 0.015 mol), P(o-tol)$_3$ (20 mg, 0.06571 mmol), Pd$_2$dba$_3$ (10 mg, 0.01169 mmol, 1 mol % Pd/Br), and two drops of aliquat 336. The mixture was placed under vacuum for 2 hours. The tube was backfilled with argon gas, and the vacuum-purge cycle was repeated 3 times. Toluene (15 mL) and water (5 mL) were added, and the mixture was stirred at 90° C. for 3 days. After addition of 4,4,5,5-tetramethyl-2-phenyl-1,3,2-dioxaborolane (550 mg, 2.7 mmol), the mixture was stirred for 8 hours at 85° C., after which, bromobenzene (0.37 mL, 3.5 mmol) was added and the mixture stirred overnight. Toluene (20 mL) was added, and the mixture was precipitated into a mixture of methanol (200 mL) and 1M HCl (25 mL). The precipitate was filtered into a 25 mm×80 mm cellulose thimble, washed 3 times with methanol (30 mL) and three times with DI water (30 mL). The precipitate was purified by soxhlet extractions: methanol (one day), acetone (one day), hexanes (one day), and chloroform (one day). The chloroform soluble fraction was treated with a spatula tip amount of diethylammonium dithiocarbonate and stirred for 10 minutes and concentrated to about 50 mL. The concentrated solution was pipetted dropwise into 200 mL of HPLC grade methanol, and the resulting precipitate was filtered on a nylon filter membrane. The polymer was then collected and dried in vacuo to yield a yellow-green solid, which forms yellow films. Yield 80% (773 mg). GPC $M_w$=17,653, $M_n$=12,008, PDI=1.47. $^1$H NMR (CDCl$_3$): δ 7.8 (br s, 2H), 7.7 (br s, 4H), 4.2 (br s, 4H), 3.58 (br s, 4H), 3.36 (br s, 4H), 2.1 (br s, 4H), 1.6-1.2 (br, 20H), 0.96 (br s, 14H) Anal. calcd. for $C_{54}H_{82}O_4S$ C, 78.40; H, 9.99, Found C, 78.79; H, 10.221.

Yellow Conjugated Polymer (ECP Yellow-1) Characterization

Figure 3:
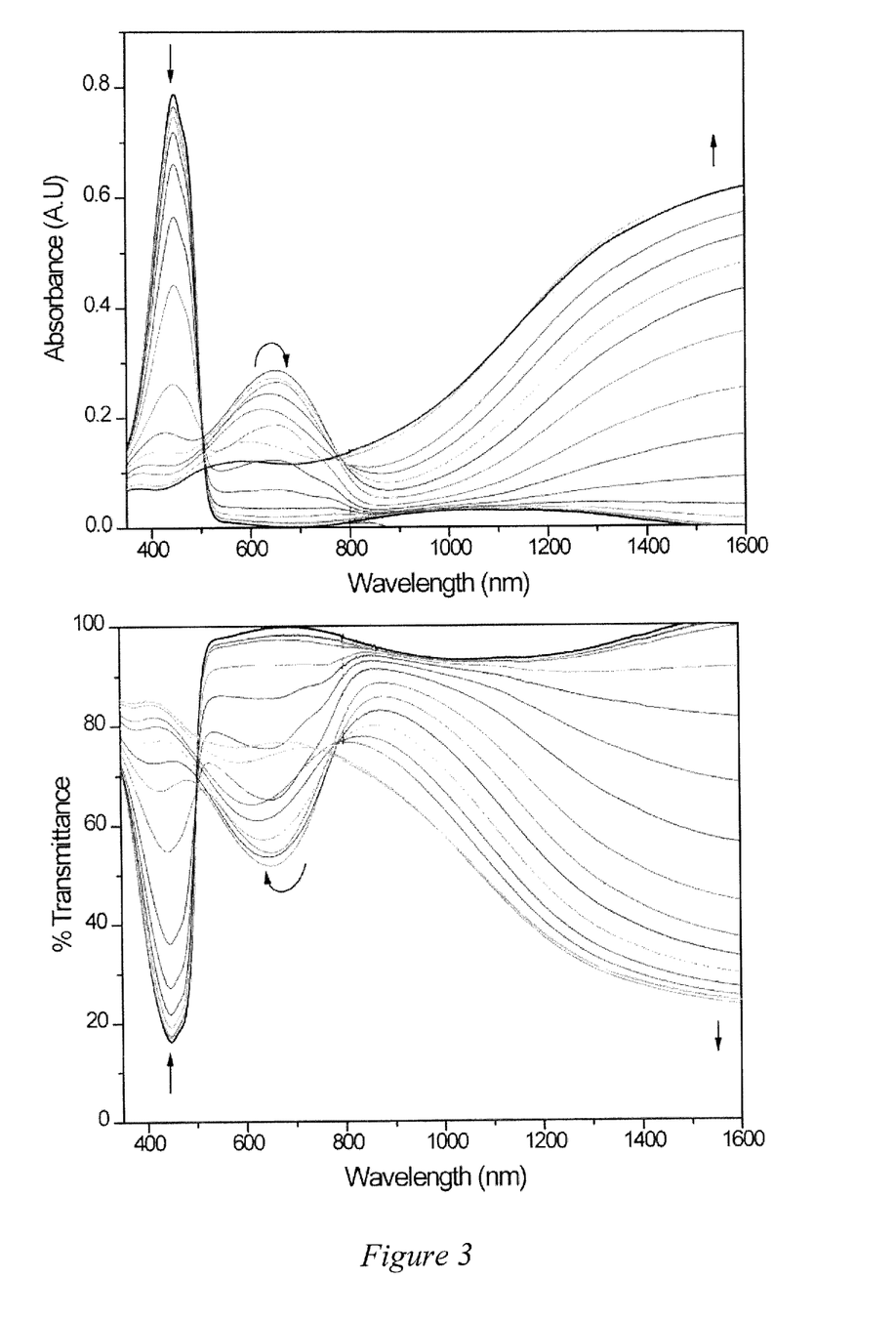
FIG. 3 shows the spectroelectrochemical analysis of ECP Yellow-1, according to an embodiment of the invention, where the polymers absorption spectra (top) and % transmittance spectra (bottom) are plotted for various applied voltages from 180 mV to 1080 mV vs. Fc/Fc$^+$ at 50 mV steps.

The yellow conjugated polymer was spray-cast onto ITO coated glass slides from a ~2 mg/mL toluene solution. Electrochemical switching by cyclic voltammetry (50 mV/s, 0.2 M lithium bistrifluoromethanesuflonamide (LiBTI)/propylene carbonate solution) between 180 mV and 1080 mV vs. Fc/Fc$^+$ was carried out until a stable and reproducible voltammogram was observed and spectroelectrochemical analysis was obtained. FIG. 3 shows the spectroelectrochemical response in absorbance (left) and percent transmittance (right). As can be seen in the absorbance spectrum in FIG. 3 (left), a sharp absorption band with $\lambda_{max}$ at 455 nm is present in the neutral state. The onset of absorption reveals a bandgap of around 2.38 eV. Upon oxidation, the intensity of absorption at 455 nm is significantly reduced, while a polaronic transition arises around 650 nm. The intensity of the polaronic transition depletes at higher oxidation levels, giving way to bipolaronic absorption with $\lambda_{max}$ greater than 1600 nm. As illustrated in the transmittance spectrum, FIG. 3 (right), the fully oxidized polymer is more than 75% transmissive across the entire visible range (400-750 nm).

Figure 4:
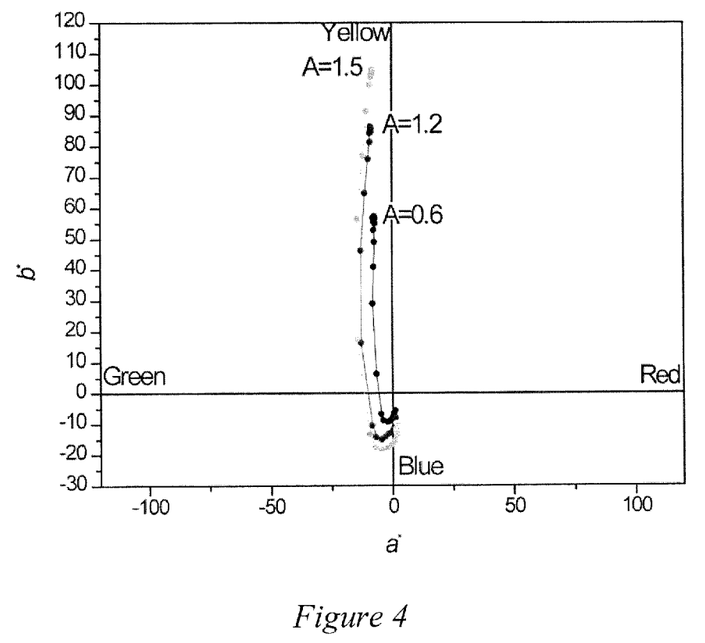
FIG. 4 shows the color change as L*a*b* values for ECP Yellow-1, according to an embodiment of the invention, where a*b* values are plotted as a function of electrochemical doping level for 50 mV steps.

To evaluate the color of the polymer films as perceived by the human eye, L*a*b* values for three polymer films were measured as a function of the electrochemical doping level, and a* b* values for each step (50 mV, 180 to 1080 mV vs Fc/Fc$^+$) are plotted in FIG. 4. Photographs of each film in the neutral and fully oxidized states corroborate the accuracy of the L*a*b* values. Extremely high b* values in the neutral state indicate that the material is a saturated yellow as viewed by the human eye, and is evident in photographs. The films also display small negative a* values indicative of a green hue, possibly due to a yellow-green emission from the polymer films. As oxidation progresses, a small negative b* value indicates that a faint blue intermediate state occurs just before doping is complete. At around 1040 mV, only a small negative b* value remains and a* values are near zero, as the highly transmissive film has a faint sky blue color.

Figure 5:
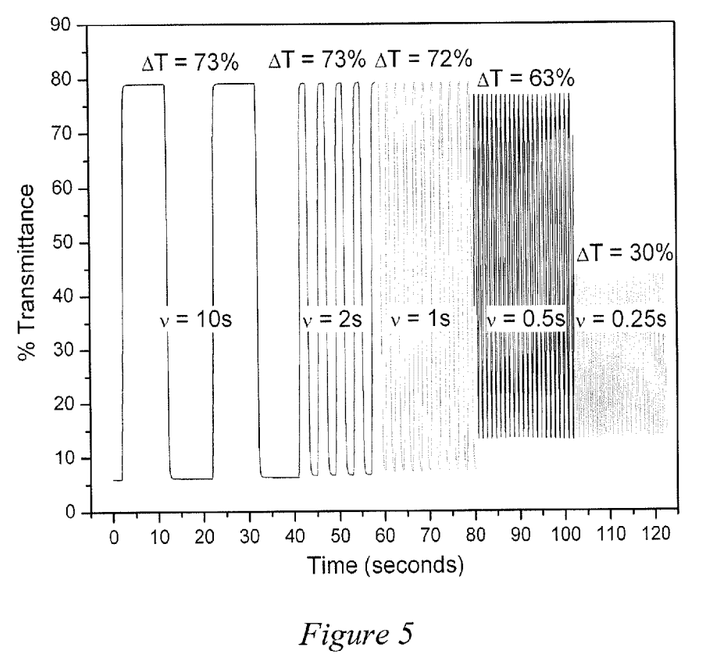
FIG. 5 shows potential square wave absorptometry plots for ECP Yellow-1, according to an embodiment of the invention, that measured at 455 nm, 180 to 1080 mV vs. Fc/Fc+ in 0.2 M Li BTI/PC solution, Pt wire CE where the switch time was increased from 10 s step for 40 s (2 cycles), 2 s step for 20 s (5 cycles), 1 s step for 30 s (15 cycles), 0.5 s step for 20 s (20 cycles), and 0.25 s step for 20 s (40 cycles).

The yellow conjugated polymer's utility for use in display type devices is indicated by the speed at which the polymer can be switched from one color state to another, as rapidly switching materials are required. FIG. 5 shows the change in absorbance at the $\lambda X_{max}$ of a spray-cast film as a function of time as potential square waves were applied. As can be seen by FIG. 5, the film exhibits an excellent contrast, 73%, at 455 nm, and is able to retain almost all of that contrast at switching rates as high as 1 second per potential step. Even at a rate of 0.5 seconds per potential, the polymer retains 63% contrast.

Potentially, by optimizing the solvent/electrolyte/conjugated polymer mixture, switching with up to 95% of contrast for a full switching rate of less than 250 milliseconds is envisioned.

Figure 6:
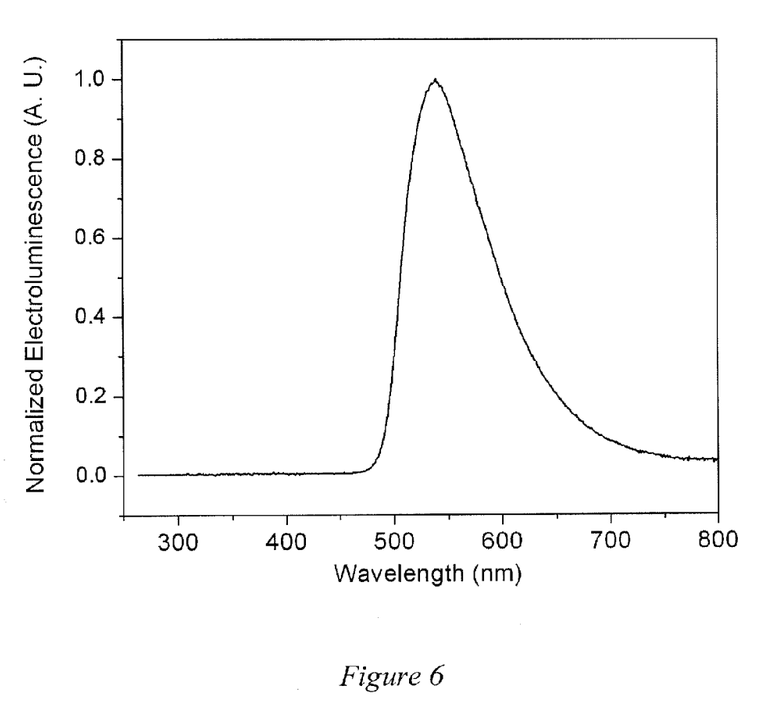
FIG. 6 shows a normalized electroluminescence spectrum for ECP Yellow-1, according to an embodiment of the invention, with an applied current density of 300 mA/cm$^2$.

To evaluate the yellow conjugated polymer for use in an electroluminescent device, a polymer light emitting diode was fabricated using a sandwich configuration of ITO/PEDOT:PSS/Yellow conjugated polymer/LiF/Al. FIG. 6 shows the electroluminescence spectrum of the yellow conjugated polymer based device at an applied current density of 300 mA/cm$^2$. As can be seen in FIG. 6, when incorporated in an electroluminescent device, the yellow polymer emits light with a maximum wavelength of around 550 nm with tailing to longer wavelengths, observable as a yellow-green color to the eye, which indicates that yellow conjugated polymers according to embodiments of the invention can be used for fabrication of dual electrochromic/electroluminescent devices.

Figure 7:
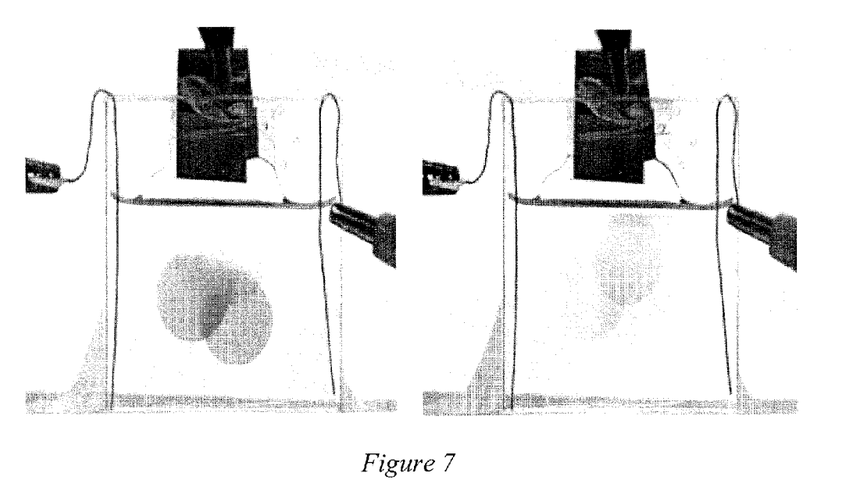
FIG. 7 (top) shows thin films deposited on transparent substrates and positioned as a Venn diagram of an exemplary yellow conjugated polymer, ECP Yellow-1, a blue conjugated polymer, and red conjugated polymer, where two overlapping films display the secondary colors green, orange, and purple, and where three overlapping films display black and the demonstration (bottom) of the films switching from their neutral colored states (left) to highly transmissive states (right) upon oxidation.

FIG. 7 shows shadow mask deposited on thin transparent films, where overlapping films of yellow conjugated polymer, blue conjugated polymer, and red conjugated polymer generate a Venn diagram by the positioning of the thin films. Combinations of such films allow a full color display, where the intensity of each of the three primaries can be controlled to generate any desired color. FIG. 7 (top) shows yellow and blue films overlapping to generate green, yellow and red films overlapping to generate orange, and red and blue films overlapping to generate purple. Where all of the colored films overlap, black is observed. FIG. 7 (bottom) shows these overlapping films in a neutral colored state (left) and these overlapping films in an oxidized transmissive state (right).

Yellow Conjugated Polymer (ECP Yellow-2) Characterization

Figure 8:
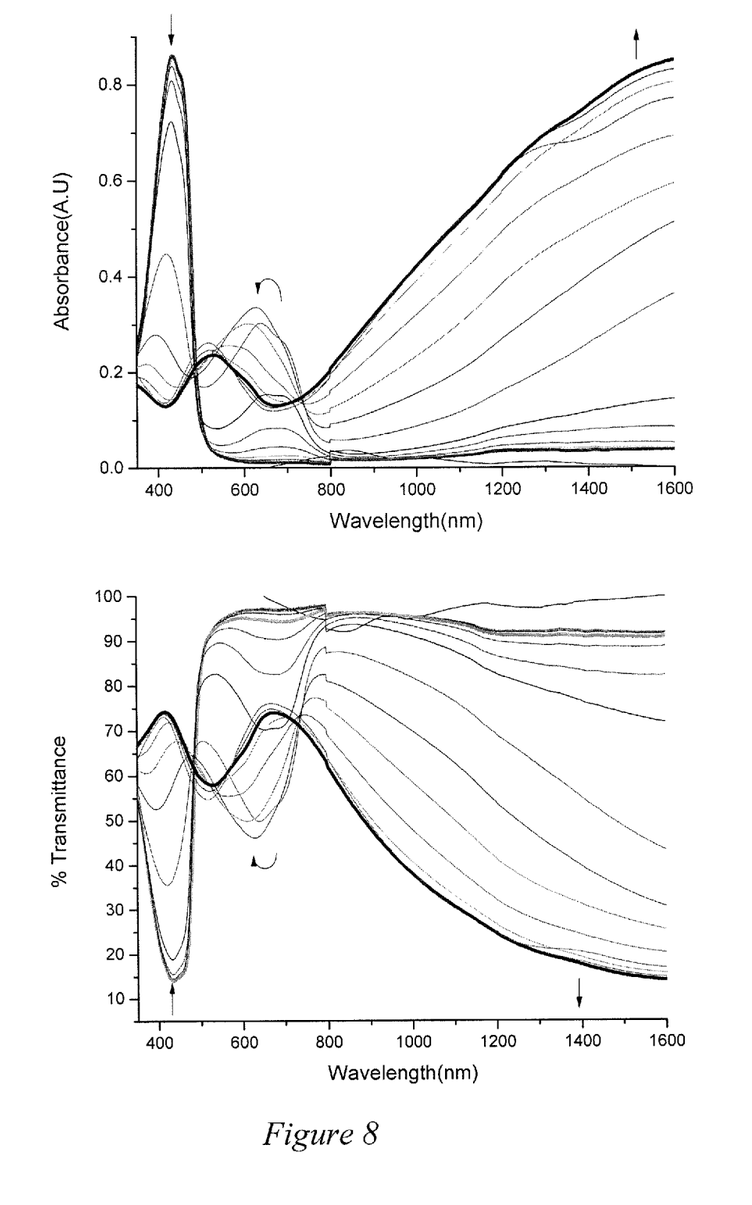
FIG. 8 shows the spectroelectrochemical analysis of ECP Yellow-2, according to an embodiment of the invention, where the polymers absorption spectra (top) and % transmittance spectra (bottom) are plotted for various applied voltages from 180 mV to 1080 mV vs. Fc/Fc$^+$ at 50 mV steps.

The yellow conjugated polymer was spray-cast onto ITO coated glass slides from a ~3 mg/mL toluene solution. Electrochemical switching by cyclic voltammetry (50 mV/s, 0.2 M lithium bistrifluoromethanesuflonamide (LiBTI)/propylene carbonate solution) between 480 mV and 960 mV vs. Fc/Fc$^+$ was carried out until a stable and reproducible voltammogram was observed, whereupon spectroelectrochemical analysis was obtained. FIG. 8 shows the spectroelectrochemical response in absorbance (top) and percent transmittance (bottom). As can be seen in the absorbance spectrum in FIG. 8 (top), a sharp absorption band with $\lambda_{max}$ at 434 nm is present in the neutral state. The onset of absorption reveals a bandgap of around 2.44 eV. Upon oxidation, the intensity of absorption at 434 nm is significantly reduced, while a polaronic transition arises around 628 nm, which blue-shifts to 526 nm over the period of oxidation. The intensity of the polaronic transition decreases at higher oxidation levels, giving way to bipolaronic absorption with a $\lambda_{max}$ greater than 1600 nm. As illustrated in the transmittance spectrum, FIG. 8 (bottom), the fully oxidized polymer exhibits ~60% transmission across the entire visible range (400-750 nm).

Figure 9:
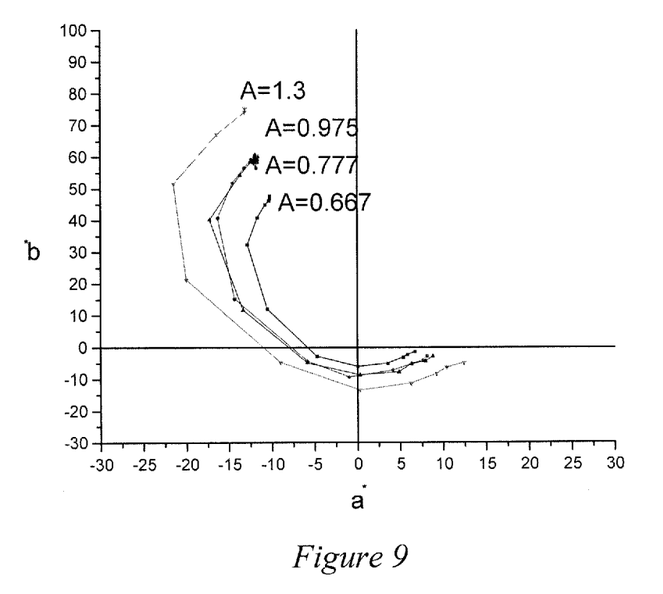
FIG. 9 shows the color change as L*a*b* values for ECP Yellow-2, according to an embodiment of the invention, where a*b* values are plotted as a function of electrochemical doping level for 50 mV steps.

T color of the ECP Yellow-2 polymer films, as perceived by the human eye, were assigned L*a*b* values for the average of three polymer films at different electrochemical doping levels. The a* b* values determined for each step of 50 mV over the range of 480 to 960 mV vs Fc/Fc$^+$), as plotted in FIG. 9. Photographs of each film in the neutral and fully oxidized states corroborate the accuracy of the L*a*b* values. High b* values in the neutral state indicate that the material is a saturated yellow as viewed by the human eye, and is evident in photographs. The films also display small negative a* values, indicative of a green hue, possibly due to a yellow-green emission from the polymer films. As oxidation progresses, a small negative b* value indicates that a faint blue intermediate state occurs just before doping is complete. At around 850 mV, only a small negative b* value remains and a* values are near zero, as the highly transmissive film has a faint sky blue color. Continuing the oxidation to 1050 mV, the films begin to exhibit a pink hue.

Figure 10:
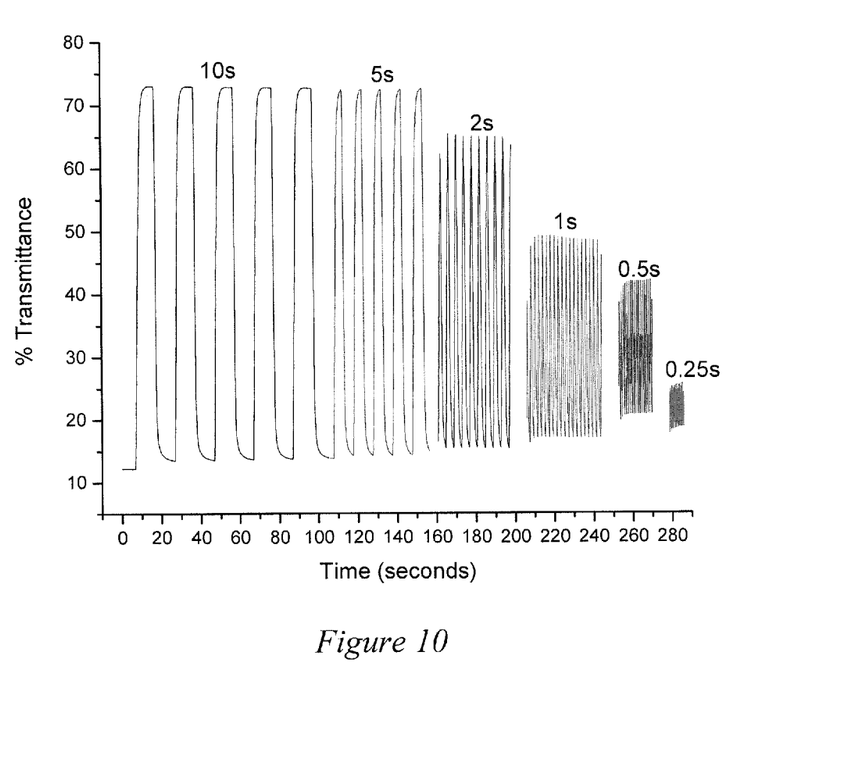
FIG. 10 shows potential square wave absorptometry plots for ECP Yellow-2, according to an embodiment of the invention, that measured at 434 nm, 180 to 1080 mV vs. Fc/Fc+ in 0.2 M Li BTI/PC solution, Pt wire CE where the switch time was increased from 10 s step for 100 s (5 cycles), 5 s step for 50 s (5 cycles), 2 s step for 40 s (10 cycles), 1 s step for 40 s (20 cycles), 0.5 s step for 20 s (20 cycles), and 0.25 s step for 10 s (20 cycles).

The yellow conjugated polymer's utility for display type devices is indicated by the speed at which the polymer can be switched from one color state to another, as rapidly switching materials are required. FIG. 10 shows the change in absorbance at $\lambda_{max}$ for a spray-cast film, as a function of time when potential square waves were applied. As can be seen by FIG. 10, the film exhibits an excellent contrast, 59.4% at 434 nm, which can be retained at switching rates as high as 2 second per potential step.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A conjugated polymer, comprising a fully conjugated polymeric sequence of at least two alternating triads comprising: a first repeating unit selected from dioxythiophene, dioxyfuran, dioxypyrrole, dioxyselenophene, or any combination thereof; and a second repeating unit selected from an aromatic molecule, thiophene, furan, pyrrole, selenophene, or any combination thereof, wherein the conjugated polymer is yellow in its neutral state, having an absorption maximum between 300 and 500 nm that upon oxidation is transmissive between 400-750 nm, wherein the conjugated polymeric sequence has the structure:

(II)

and, optionally, a second conjugated polymeric sequence of the structure:

(I)

where A is an aromatic unit, thiophene unit, furan unit, pyrrole unit, selenophene unit, or any combination thereof; n is 2 to 200,000; X is S, Se, O, or NR; x is 0 or 1; y is 0 or 1; R, R$^9$, and R$^{10}$ are independently H, C$_1$-C$_{30}$ alkyl, C$_2$-C$_{30}$ alkenyl, C$_2$-C$_{30}$ alkynyl, C$_6$-C$_{14}$ aryl, C$_7$-C$_{30}$ arylalkyl, C$_8$-C$_{30}$ arylalkenyl, C$_8$-C$_{30}$ arylalkynyl, C$_2$-C$_{30}$ alkylester, C$_7$-C$_{15}$ arylester, C$_8$-C$_{30}$ alkylarylester, C$_3$-C$_{30}$ alkenylester, C$_3$-C$_{30}$ alkynylester, NH$_2$, C$_1$-C$_{30}$ alkylamino, C$_6$-C$_{14}$ arylamino, C$_7$-C$_{30}$ (arylalkyl)amino, C$_2$-C$_{30}$ alkenylamino, C$_2$-C$_{30}$ alkynylamino, C$_8$-C$_{30}$ (arylalkenyl)amino, C$_8$-C$_{30}$ (arylalkynyl)amino, C$_2$-C$_{30}$ dialkylamino, C$_{12}$-C$_{28}$ diarylamino, C$_4$-C$_{30}$ dialkenylamino, C$_4$-C$_{30}$ dialkynylamino, C$_7$-C$_{30}$ aryl(alkyl)amino, C$_7$-C$_{30}$ di(arylalkyl)amino, C$_8$-C$_{30}$ alkyl(arylalkyl)amino, C$_{15}$-C$_{30}$ aryl(arylalkyl)amino, C$_8$-C$_{30}$ alkenyl(aryl)amino, C$_8$-C$_{30}$ alkynyl(aryl)amino C(O)NH$_2$ (amido), C$_2$-C$_{30}$ alkylamido, C$_7$-C$_{14}$ arylamido, C$_8$-C$_{30}$ (arylalkyl)amido, C$_2$-C$_{30}$ dialkylamido, C$_{12}$-C$_{28}$ diarylamido, C$_8$-C$_{30}$ aryl(alkyl)amido, C$_{15}$-C$_{30}$ di(arylalkyl)amido, C$_9$-C$_{30}$ alkyl(arylalkyl)amido, C$_{16}$-C$_{30}$ aryl(arylalkyl)amido, thiol, C$_1$-C$_{30}$ alkylhydroxy, C$_6$-C$_{14}$ arylhydroxy, C$_7$-C$_{30}$ arylalkylhydroxy, C$_3$-C$_{30}$ alkenylhydroxy, C$_3$-C$_{30}$ alkynylhydroxy, C$_8$-C$_{30}$ arylalkenylhydroxy, C$_8$-C$_{30}$ aryl alkynylhydroxy, C$_3$-C$_{30}$ polyether, C$_3$-C$_{30}$ polyetherester, C$_3$-C$_{30}$ polyester C$_3$-C$_{30}$ polyamino, C$_3$-C$_{30}$ polyaminoamido, C$_3$-C$_{30}$ polyaminoether, C$_3$-C$_{30}$ polyaminoester, C$_3$-C$_{30}$ polyamidoester, C$_3$-C$_{30}$ alkylsulfonic acid, C$_3$-C$_{30}$ alkylsulfonate salt, C$_1$-C$_{30}$ carboxylate salt, C$_1$-C$_{30}$ thiocarboxylate salt, C$_1$-C$_{30}$ dithiocarboxylate salt, or C$_3$-C$_{30}$ alkyl C$_1$-C$_4$ trialkyammonium salt and R$^1$, R$^2$, R$^3$, R$^4$, R$^5$, R$^6$, R$^7$ and R$^8$ are independently H, C$_1$-C$_{30}$ alkyl, C$_2$-C$_{30}$ alkenyl, C$_2$-C$_{30}$ alkynyl, C$_6$-C$_{14}$ aryl, C$_7$-C$_{30}$ arylalkyl, C$_8$-C$_{30}$ arylalkenyl, C$_8$-C$_{30}$ arylalkynyl, hydroxy, C$_1$-C$_{30}$ alkoxy, C$_6$-C$_{14}$ aryloxy, C$_7$-C$_{30}$ arylalkyloxy, C$_2$-C$_{30}$ alkenyloxy, C$_2$-C$_{30}$ alkynyloxy, C$_8$-C$_{30}$ aryl alkenyloxy, C$_8$-C$_{30}$ arylalkynyloxy, CO$_2$H, C$_2$-C$_{30}$ alkylester, C$_7$-C$_{15}$ arylester, C$_8$-C$_{30}$ alkylarylester, C$_3$-C$_{30}$ alkenylester, C$_3$-C$_{30}$ alkynylester, NH$_2$, C$_1$-C$_{30}$ alkylamino, C$_6$-C$_{14}$ arylamino, C$_7$-C$_{30}$ (arylalkyl)amino, C$_2$-C$_{30}$ alkenylamino, C$_2$-C$_{30}$ alkynylamino, C$_8$-C$_{30}$ (arylalkenyl)amino, C$_8$-C$_{30}$ (arylalkynyl)amino, C$_2$-C$_{30}$ dialkylamino, C$_{12}$-C$_{28}$ diarylamino, C$_4$-C$_{30}$ dialkenylamino, C$_4$-C$_{30}$ dialkynylamino, C$_7$-C$_{30}$ aryl(alkyl)amino, C$_7$-C$_{30}$ di(arylalkyl)amino, C$_8$-C$_{30}$ alkyl(arylalkyl)amino, C$_{15}$-C$_{30}$ aryl(arylalkyl)amino, C$_8$-C$_{30}$ alkenyl(aryl)amino, C$_8$-C$_{30}$ alkynyl(aryl)amino, C(O)NH$_2$ (amido), C$_2$-C$_{30}$ alkylamido, C$_7$-C$_{14}$ arylamido, C$_8$-C$_{30}$ (arylalkyl)amido, C$_2$-C$_{30}$ dialkylamido, C$_{12}$-C$_{28}$ diarylamido, C$_8$-C$_{30}$ aryl(alkyl)amido, C$_{15}$-C$_{30}$ di(arylalkyl)amido, C$_9$-C$_{30}$ alkyl(arylalkyl)amido, C$_{16}$-C$_{30}$ aryl(arylalkyl)amido, thiol, C$_1$-C$_{30}$ hydroxyalkyl, C$_6$-C$_{14}$ hydroxyaryl, C$_7$-C$_{30}$ hydroxyarylalkyl, C$_3$-C$_{30}$ hydroxyalkenyl, C$_3$-C$_{30}$ hydroxyalkynyl, C$_8$-C$_{30}$ hydroxyarylalkenyl, C$_8$-C$_{30}$ hydroxyarylalkynyl, C$_3$-C$_{30}$ polyether, C$_3$-C$_{30}$ polyetherester, C$_3$-C$_{30}$ polyester, C$_3$-C$_{30}$ polyamino, C$_3$-C$_{30}$ polyaminoamido, C$_3$-C$_{30}$ polyaminoether, C$_3$-C$_{30}$ polyaminoester, C$_3$-C$_{30}$ polyamidoester, C$_3$-C$_{30}$ alkylsulfonic acid, C$_3$-C$_{30}$ alkylsulfonate salt, C$_1$-C$_{30}$ carboxylate salt, C$_1$-C$_{30}$ thiocarboxylate salt, C$_1$-C$_{30}$ dithiocarboxylate salt or C$_3$-C$_{30}$ alkylC$_1$-C$_4$ trialkyammonium salt, and wherein the aromatic unit, thiophene unit, furan unit, pyrrole unit comprises:

-continued where: X is NR', PR', S, O, Se, SOx, CR2, SiR'2, GeR'2, or BR', where x=1 or 2; X' is NR', O, Se, or S; where R' is H, C1-C30 alkyl, C2-C30 alkenyl, C2-C30 alkynyl, C6-C14 aryl, C7-C30 arylalkyl, C8-C30 arylalkenyl, C8-C30 arylalkynyl, C1-C30 hydroxyalkyl, C6-C14 hydroxyaryl, C7-C30 hydroxyarylalkyl, C3-C30 hydroxyalkenyl, C3-C30 hydroxyalkynyl, C8-C30 hydroxyarylalkenyl, C8-C30 hydroxyarylalkynyl, C3-C30 polyether, C3-C30 polyetherester, C3-C30 polyester, C3-C30 polyamino, C3-C30 polyaminoamido, C3-C30 polyaminoether, C3-C30 polyaminoester, C3-C30 polyamidoester, C3-C30alkylsulfonic acid, C3-C30alkylsulfonate salt, C1-C30 alkylcarboxylate salt, C1-C30 alkylthiocarboxylate salt, C1-C30 alkyldithiocarboxylate salt or C3-C30 alkyl C1-C4 trialkyammonium salt; R" is independently H, C1-C30 alkyl, C3-C30 alkenyl, C2-C30 alkynyl, C6-C14 aryl, C7-C30 arylalkyl, C8-C30 arylalkenyl, C8-C30 arylalkynyl; and R is independently H, C1-C30 alkyl, C2-C30 alkenyl, C2-C30 alkynyl, C6-C14 aryl, C7-C30 arylalkyl, C8-C30 arylalkenyl, C8-C30 arylalkynyl, hydroxy, C1-C30 alkoxy, C6-C14 aryloxy, C7-C30 arylalkyloxy, C2-C30 alkenyloxy, C2-C30 alkynyloxy, C8-C30 arylalkenyloxy, C8-C30 arylalkynyloxy, CO2H, C2-C30 alkylester, C7-C15 arylester, C8-C30 alkylarylester, C3-C30 alkenylester, C3-C30 alkynylester, NH2, C1-C30 alkylamino, C6-C14 arylamino, C7-C30 (arylalkyl)amino, C2-C30 alkenylamino, C2-C30 alkynylamino, C8-C30 (arylalkenyl)amino, C8-C30 (arylalkynyl)amino, C2-C30 dialkylamino, C12-C28 diarylamino, C4-C30 dialkenylamino, C4-C30 dialkynylamino, C7-C30 aryl(alkyl)amino, C7-C30 di(arylalkyl)amino, C8-C30 alkyl(arylalkyl)amino, C15-C30 aryl(arylalkyl) amino, C8-C30 alkenyl(aryl)amino, C8-C30 alkynyl(aryl) amino C(O)NH2 (amido), C2-C30 alkylamido, C7-C14 arylamido, C8-C30 (arylalkyl)amido, C2-C30 dialkylamido, C12-C28 diarylamido, C8-C30 aryl(alkyl)amido, C15-C30 di(arylalkyl)amido, C9-C30 alkyl(arylalkyl)amido, C16-C30 aryl(arylalkyl)amido, thiol, C1-$C_{30}$ hydroxyalkyl, C6-C14 hydroxyaryl, C7-C30 hydroxyarylalkyl, C3-C30 hydroxyalkenyl, C3-C30 hydroxyalkynyl, C8-C30 hydroxyarylalkenyl, C8-C30 hydroxyarylalkynyl, C3-C30 polyether, C3-C30 polyetherester, C3-C30 polyester, C3-C30 polyamino, C3-C30 polyaminoamido, C3-C30 polyaminoether, C3-C30 polyaminoester, C3-C30 polyamidoester, C3-C30 alkylsulfonic acid, C3-C30alkylsulfonate salt, C1-C30 carboxylate salt, C1-C30 thiocarboxylate salt, C1-C30 dithiocarboxylate salt, or C3-C30 alkylC1-C4 trialkyammonium salt.

2. The conjugated polymer of claim 1, wherein the fully conjugated polymeric sequence is: an alternating copolymer; a portion of a random, block, graft, branched, hyperbranched, or dendritic copolymer; or a portion of a network.

3. The conjugated polymer of claim 1, wherein the conjugated polymer or a polymeric precursor of the conjugated polymer is soluble in at least one solvent.

4. The conjugated polymer of claim 3, wherein the solvent comprises toluene, chloroform, dichloromethane, hexanes, tetrahydrofuran, chlorobenzene, water, ethanol, or other solvent.

5. The conjugated polymer of claim 1, wherein a thin film comprising the conjugated polymer in the neutral state displays a transmittance of less than about 40% between 400 nm and 500 nm and greater than about 90% transmittance from 600 nm-750 nm.

6. The conjugated polymer of claim 1, wherein a thin film comprising the conjugated polymer in the oxidized state displays a transmittance of more than about 70% between 400 and 750 nm.

7. The conjugated polymer of claim 1, wherein the conjugated polymer is electrochromic or electroluminescent.

8. A method for the preparation of the conjugated polymer of claim 1, comprising:
   combining in one or more solvents a plurality of one or more nucleophilic monomeric aromatic units, thiophene units, furan units, pyrrole units, selenophene units or combination thereof that are disubstituted with groups comprising tin, boron, zinc, and a plurality of one or more electrophilic monomeric dioxyhetereocyclic units having a pair of leaving groups; or
   combining in one or more solvents a plurality of one or more nucleophilic monomeric dioxyheterocyclic units that are disubstituted with groups comprising tin, boron, zinc, silicon, or magnesium and a plurality of one or more electrophilic monomeric aromatic units, thiophene units, furan units, pyrrole units, selenophene units, or combination thereof having a pair of leaving groups;
   optionally adding a catalyst; and
   cross-coupling the nucleophilic monomeric units with the electrophilic monomeric units to yield the conjugated polymer or a precursor of the conjugated polymer.

9. The method of claim 8, wherein the conjugated polymer is soluble in at least one solvent.

10. The method of claim 8, wherein the leaving group comprises halogen, triflate, tosylate, nosylate, trifluoroacetate, or mesylate.

11. The method of claim 8, wherein the halogen comprises bromine.

12. The method of claim 8, wherein the catalyst comprises a palladium or nickel comprising compound.

13. The method of claim 8, wherein said cross-coupling comprises a Stille coupling, Kumada coupling, Hiyama coupling, Negishi coupling, inverse Suzuki coupling, or Grignard methathesis (GRIM).

14. An electrochromic device (ED), comprising the conjugated polymer of claim 1 and at least one non-yellow conjugated polymer that displays a primary subtractive color in a neutral state and is transmissive in an oxidized state.

15. The ED of claim 14, wherein a plurality of the non-yellow conjugated polymers display red and blue in the neutral state.

16. The ED of claim 14, wherein a plurality of the non-yellow conjugated polymers display magenta and cyan in the neutral state.

17. The ED of claim 14, wherein the device is transmissive or reflective.

18. A method of preparing an ED comprising the conjugated polymer of claim 1, comprising deposition of the conjugated polymer from solution onto a surface.

19. The method of claim 18, wherein deposition comprises spraying, printing, slot die coating, roll-to-roll coating, or electrostatic adsorption.

* * * * *

UNITED STATES PATENT AND TRADEMARK OFFICE
CERTIFICATE OF CORRECTION

PATENT NO. : 8,519,090 B2
APPLICATION NO. : 13/775961
DATED : August 27, 2013
INVENTOR(S) : Amb et al.

It is certified that error appears in the above-identified patent and that said Letters Patent is hereby corrected as shown below:

In the Specifications

Column 7,
Line 2, "$C_2$-$C_{14}$" should read --$CO_2H$--.
Line 49, "$R^3$=$R^4$H" should read --$R^3 = R^4 \neq H$--.

Column 10,
Line 27, "PropOT-A" should read --ProDOT-A--.

Column 11,
Line 38, "The chlorofolln" should read --The chloroform--.

Column 12,
Line 62, "$\lambda X_{max}$" should read --$\lambda_{max}$--.

Signed and Sealed this
Tenth Day of December, 2013

Margaret A. Focarino
*Commissioner for Patents of the United States Patent and Trademark Office*